US009828414B2

(12) United States Patent
Steigerwald et al.

(10) Patent No.: US 9,828,414 B2
(45) Date of Patent: Nov. 28, 2017

(54) PR13.5 PROMOTER FOR ROBUST T-CELL AND ANTIBODY RESPONSES

(71) Applicant: Bavarian Nordic A/S, Kvistgaard (DK)

(72) Inventors: Robin Steigerwald, Munich (DE); Kay Brinkmann, Munich (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 0 days.

(21) Appl. No.: 14/437,939

(22) PCT Filed: Oct. 28, 2013

(86) PCT No.: PCT/EP2013/003239
§ 371 (c)(1),
(2) Date: Apr. 23, 2015

(87) PCT Pub. No.: WO2014/063832
PCT Pub. Date: May 1, 2014

(65) Prior Publication Data
US 2015/0299267 A1    Oct. 22, 2015

Related U.S. Application Data

(60) Provisional application No. 61/719,429, filed on Oct. 28, 2012.

(51) Int. Cl.
*C07K 14/005* (2006.01)
*C12N 7/00* (2006.01)
*C12N 15/86* (2006.01)
*A61K 39/00* (2006.01)

(52) U.S. Cl.
CPC .............. *C07K 14/005* (2013.01); *C12N 7/00* (2013.01); *C12N 15/86* (2013.01); *A61K 2039/5256* (2013.01); *A61K 2039/572* (2013.01); *C12N 2710/24122* (2013.01); *C12N 2710/24143* (2013.01); *C12N 2830/60* (2013.01)

(58) Field of Classification Search
None
See application file for complete search history.

(56) References Cited

FOREIGN PATENT DOCUMENTS

JP          2008301792      12/2008
WO    WO 2006/073431 A2    7/2006

OTHER PUBLICATIONS

Wennier, Kay et al. "A Novel Naturally Occurring Tandem Promoter in Modified Vaccinai Virus Ankara . . . " PLOS One 8 (8): e73511 (2013).
Wachsman et al., "Antigen Presenting Capacity of Epidermal Cells Infected with Vaccinia Virus Recombinants Containing the Herpes Simplex Virus Glycoprotein D, and Protective Immunity" J. Gen. Virol. 70:2513-20 (1989).
Tine et al., "NYVAC-Pf7: a poxvirus-vectored, multiantigen multistage vaccine candidate for Plasmodium falciparum malaria" Infect. Immun, 54: 3833 (1996).
Perkus et al., "Cloning and Expression of Foreign Genes in Vaccinia Virus, Using a Host Range Selection System" Journal of Virology, 63: 3829-3836 (1989).
Moutaffsi et al. "Uncovering the interplay between CD8, CD4 and antibody responses to complex pathogens", Future Microbiol. 5:221-239 (2010).
Moutaffsi et al. "Vaccinia Virus-Specific CD4 T cell Responses Target a Set of Antigens Largely Distinct from Those Targeted by CD8 T Cell Responses." Journal of Immunology 178: 6814-6820 (2007).
Kotwal et al. "Analysis of Large Cluster of Nonessential Genes Deleted from a Vaccinia Virus Terminal Transposition Mutant" Virology, 167: 524-37 (1988).
Gen Bank Accession No. AY243312 dated Mar. 14, 2006.
Davison et al. "Structure of Vaccinia Virus Early Promoters" J. Mol. Biol. 210: 749-769 (1989).
Baur et al. "Immediate-Early Expression of a Recombinant Antigen by Modified Vaccinia Virus Ankara Breaks the Immunodominance Strong Vector-Specific B8R antigen in Acute and Memory CD8 T-cell responses" Journal of Virology, 84: 8743-52 (2010).
Written Opinion of the International Search Authority for PCT/EP2013/003239, dated Jan. 17, 2014.
International Search Report of the International Search Authority for PCT/EP2013/003239, dated Jan. 17, 2014.
Orubu et al., Expression and Cellular Immunogeneicity of a Transgenic Antigen Driven by Endogenous Poxviral Early promoters at their Authentic Loc in MVA, PLOS one, vol. 7, Issue 6 (Jun. 2012).

*Primary Examiner* — Benjamin P Blumel

(57) ABSTRACT

The invention encompasses recombinant poxviruses, preferably modified Vaccinia Ankara (MVA) viruses, comprising a Pr13.5 promoter operably linked to a nucleotide sequence encoding an antigen and uses thereof. The invention is drawn to compositions and methods for the induction of strong CD8 T cell and antibody responses to a specific antigen(s) by administering one or more immunizations of the recombinant MVA to a mammal, preferably a human.

4 Claims, 18 Drawing Sheets

15973 TAGACGACAT GATAGAGGAG GTATCCATTG ACGATAATCG TTTATCAACA CTACCGTTAG AAATTAGACA TTTGATTTTC TCGTACGCGT TCCT<u>TAAAA</u>

15873 <u>ATAGAAACTA TAATCATATA ATAGTGTAGG TTGGTAGTA</u>T TGCTCTTGTG ACTAGAGACT TTAGT TAAGG TACTG<u>TAAAA ATAGAAACTA TAATCATATA</u>

Pr13.5-long
Pr13.5-short

15773 <u>ATAGTGTAGG TTGGTAGT</u>G GGTACTCGTG ATTAATTTTA TTGTTAAACT TGTCCTTAAG TCTTATTAAT <u>ATG</u>

Figure 2

| Promoter | Fold over PrS | | |
|---|---|---|---|
| | 1st immunization | 2nd immunization | 3rd immunization |
| PrS | 1.0 | 1.0 | 1.0 |
| Pr13.5-short | 0.1 | 0.6 | 0.5 |
| Pr13.5-long | 1.6 | 2.8 | 1.3 |
| Pr7.5 opt + spacer | 0.0 | 0.0 | 0.2 |
| MVA50L + PrSSL | 0.1 | 0.2 | 0.1 |
| MVA170 + PrSSL | 0.0 | 0.8 | 0.5 |

Figure 7B

| Query | 1 | TAAAAATAGAAACTATAATCATATAATAGTGTAGGTTGGTAGTA | 44 |
|---|---|---|---|
| 383866716 | 20492 | ............................................ | 20449 |
| 383866716 | 20410 | ........................-................... | 20369 |
| 373449558 | 15874 | ............................................ | 15831 |
| 373449558 | 15954 | ............................................ | 15911 |
| 373449318 | 15878 | ............................................ | 15835 |
| 373449318 | 15958 | ............................................ | 15915 |
| 373449318 | 182742 | ............................................ | 182785 |
| 373449318 | 182822 | ............................................ | 182865 |
| 373449076 | 15864 | ............................................ | 15821 |
| 373449076 | 15944 | ............................................ | 15901 |
| 373449076 | 182666 | ............................................ | 182709 |
| 373449076 | 182746 | ............................................ | 182789 |
| 373448847 | 15961 | ............................................ | 15918 |
| 373448847 | 16041 | ............................................ | 15998 |
| 373448604 | 15956 | ............................................ | 15913 |
| 373448604 | 16036 | ............................................ | 15993 |
| 373448604 | 182785 | ............................................ | 182828 |
| 373448604 | 182865 | ............................................ | 182908 |
| 373448367 | 15865 | ............................................ | 15822 |
| 373448367 | 15945 | ............................................ | 15902 |
| 373448367 | 182603 | ............................................ | 182646 |
| 373448367 | 182683 | ............................................ | 182726 |
| 373448133 | 15832 | ............................................ | 15789 |
| 373448133 | 15912 | ............................................ | 15869 |
| 373447891 | 15957 | ............................................ | 15914 |
| 373447891 | 16037 | ............................................ | 15994 |
| 373447891 | 182788 | ............................................ | 182831 |
| 373447891 | 182868 | ............................................ | 182911 |
| 373447653 | 15866 | ............................................ | 15823 |
| 373447653 | 15946 | ............................................ | 15903 |
| 373447653 | 182609 | ............................................ | 182652 |
| 373447653 | 182689 | ............................................ | 182732 |
| 373447414 | 15833 | ............................................ | 15790 |
| 373447414 | 15913 | ............................................ | 15870 |
| 373447414 | 182552 | ............................................ | 182595 |
| 373447414 | 182632 | ............................................ | 182675 |
| 373447175 | 15860 | ............................................ | 15817 |
| 373447175 | 15940 | ............................................ | 15897 |
| 373447175 | 182579 | ............................................ | 182622 |
| 373447175 | 182659 | ............................................ | 182702 |
| 325558812 | 28969 | ............................................ | 28926 |
| 325558812 | 28889 | ................................T........... | 28847 |
| 325558595 | 30006 | ............................................ | 29963 |
| 325558595 | 29924 | ............................................ | 29884 |
| 325558381 | 27900 | ............................................ | 27857 |
| 325558381 | 27817 | ........................C................... | 27777 |
| 325558165 | 30228 | ............................................ | 30185 |
| 325558165 | 30148 | ................................T........... | 30106 |
| 325557951 | 27554 | ............................................ | 27511 |
| 325557951 | 27472 | ........................C................... | 27432 |
| 167412463 | 12323 | ............................................ | 12280 |
| 167412463 | 12403 | ............................................ | 12360 |

FIGURE 8A

| | | | |
|---|---|---|---|
| 160857876 | 13468 | ............................................................. | 13425 |
| 160857876 | 13548 | ............................................................. | 13505 |
| 149786253 | 9445 | ............................................................. | 9402 |
| 149786253 | 9525 | ............................................................. | 9482 |
| 119352440 | 15780 | ............................................................. | 15737 |
| 119352440 | 15860 | ............................................................. | 15817 |
| 90819652 | 18373 | ............................................................. | 18330 |
| 90819652 | 18453 | ............................................................. | 18410 |
| 115607420 | 9159 | ............................................................. | 9116 |
| 115607420 | 9239 | ............................................................. | 9196 |
| 115607419 | 9159 | ............................................................. | 9116 |
| 115607419 | 9239 | ............................................................. | 9196 |
| 115607418 | 9359 | ............................................................. | 9316 |
| 115607418 | 9439 | ............................................................. | 9396 |
| 115607417 | 9359 | ............................................................. | 9316 |
| 115607417 | 9439 | ............................................................. | 9396 |
| 111184167 | 24167 | ............................................................. | 24124 |
| 111184167 | 24247 | ..........................T.......................... | 24204 |
| 109726482 | 7441 | ............................................................. | 7398 |
| 109726482 | 7517 | ............................................................. | 7474 |
| 109726279 | 7443 | ............................................................. | 7400 |
| 109726279 | 7519 | ............................................................. | 7476 |
| 109726076 | 7652 | ............................................................. | 7609 |
| 109726076 | 7728 | ............................................................. | 7685 |
| 109725872 | 7441 | ............................................................. | 7398 |
| 109725872 | 7517 | ............................................................. | 7474 |
| 109725669 | 7441 | ............................................................. | 7398 |
| 109725669 | 7517 | ............................................................. | 7474 |
| 109725465 | 7441 | ............................................................. | 7398 |
| 109725465 | 7517 | ............................................................. | 7474 |
| 109725262 | 7511 | ............................................................. | 7468 |
| 109725262 | 7587 | ............................................................. | 7544 |
| 109725056 | 7650 | ............................................................. | 7607 |
| 109725056 | 7726 | ............................................................. | 7683 |
| 109724854 | 7371 | ............................................................. | 7328 |
| 109724854 | 7447 | ............................................................. | 7404 |
| 109724650 | 7785 | ............................................................. | 7742 |
| 109724650 | 7861 | ............................................................. | 7818 |
| 109724445 | 7649 | ............................................................. | 7606 |
| 109724445 | 7725 | ............................................................. | 7682 |
| 109724243 | 7579 | ............................................................. | 7536 |
| 109724243 | 7655 | ............................................................. | 7612 |
| 109724039 | 7441 | ............................................................. | 7398 |
| 109724039 | 7517 | ............................................................. | 7474 |
| 94490104 | 7441 | ............................................................. | 7398 |
| 94490104 | 7517 | ............................................................. | 7474 |
| 94489896 | 7422 | ............................................................. | 7379 |
| 94489896 | 7498 | ............................................................. | 7455 |
| 94489695 | 7441 | ............................................................. | 7398 |
| 94489695 | 7517 | ............................................................. | 7474 |
| 94489496 | 7441 | ............................................................. | 7398 |
| 94489496 | 7517 | ............................................................. | 7474 |

FIGURE 8B

| | | | |
|---|---|---|---|
| 94489293 | 7372 | .................................A................................ | 7329 |
| 94489293 | 7448 | ................................................................... | 7405 |
| 94489094 | 7581 | ................................................................... | 7538 |
| 94489094 | 7657 | ................................................................... | 7614 |
| 94488894 | 7443 | ................................................................... | 7400 |
| 94488894 | 7519 | ................................................................... | 7476 |
| 94488693 | 7722 | ................................................................... | 7679 |
| 94488693 | 7798 | ................................................................... | 7755 |
| 94488492 | 7653 | ................................................................... | 7610 |
| 94488492 | 7729 | ................................................................... | 7686 |
| 94488292 | 6666 | ................................................................... | 6623 |
| 94488292 | 6742 | ................................................................... | 6699 |
| 94488092 | 6666 | ................................................................... | 6623 |
| 94488092 | 6742 | ................................................................... | 6699 |
| 94487887 | 7441 | ................................................................... | 7398 |
| 94487887 | 7517 | ................................................................... | 7474 |
| 94487685 | 7444 | ................................................................... | 7401 |
| 94487685 | 7520 | ................................................................... | 7477 |
| 94487484 | 7443 | ................................................................... | 7400 |
| 94487484 | 7519 | ................................................................... | 7476 |
| 94487278 | 7449 | ................................................................... | 7406 |
| 94487278 | 7373 | ........A.......................................................... | 7330 |
| 94487078 | 7442 | ................................................................... | 7399 |
| 94487078 | 7518 | ................................................................... | 7475 |
| 94486875 | 7579 | ................................................................... | 7536 |
| 94486875 | 7655 | ................................................................... | 7612 |
| 94486673 | 7430 | ................................................................... | 7387 |
| 94486673 | 7507 | ................................................................... | 7463 |

\
|
A

| | | | |
|---|---|---|---|
| 94486471 | 7431 | ................................................................... | 7388 |
| 94486471 | 7508 | ................................................................... | 7464 |

\
|
A

| | | | |
|---|---|---|---|
| 94486268 | 7442 | ................................................................... | 7399 |
| 94486268 | 7519 | ................................................................... | 7475 |

\
|
A

| | | | |
|---|---|---|---|
| 94486065 | 7442 | ................................................................... | 7399 |
| 94486065 | 7519 | ................................................................... | 7475 |

\
|
A

| | | | |
|---|---|---|---|
| 94485863 | 7441 | ................................................................... | 7398 |
| 94485863 | 7517 | ................................................................... | 7474 |
| 94485659 | 7441 | ................................................................... | 7398 |
| 94485659 | 7517 | ................................................................... | 7474 |
| 94485457 | 7863 | ................................................................... | 7820 |
| 94485457 | 7939 | ................................................................... | 7896 |

FIGURE 8C

| | | | |
|---|---|---|---|
| 94485254 | 7863 | .................................................. | 7820 |
| 94485254 | 7939 | .................................................. | 7896 |
| 94485053 | 7648 | .................................................. | 7605 |
| 94485053 | 7724 | .................................................. | 7681 |
| 94484855 | 7648 | .................................................. | 7605 |
| 94484855 | 7724 | .................................................. | 7681 |
| 94484657 | 7648 | .................................................. | 7605 |
| 94484657 | 7724 | .................................................. | 7681 |
| 94484460 | 7648 | .................................................. | 7605 |
| 94484460 | 7724 | .................................................. | 7681 |
| 94484252 | 7422 | .................................................. | 7379 |
| 94484252 | 7498 | .................................................. | 7455 |
| 94484050 | 7450 | .................................................. | 7407 |
| 94484050 | 7526 | .................................................. | 7483 |
| 94483847 | 7450 | .................................................. | 7407 |
| 94483847 | 7526 | .................................................. | 7483 |
| 94483641 | 7510 | .................................................. | 7467 |
| 94483641 | 7586 | .................................................. | 7543 |
| 90660453 | 12795 | .................................................. | 12752 |
| 90660453 | 12719 | .....................................-........T......... | 12677 |
| 90660233 | 28919 | .................................................. | 28876 |
| 90660233 | 28837 | .................................................. | 28797 |
| 38348858 | 16052 | .................................................. | 16009 |
| 38348858 | 16132 | .................................................. | 16089 |
| 38348858 | 182942 | .................................................. | 182985 |
| 38348858 | 183022 | .................................................. | 183065 |
| 37551435 | 16065 | .................................................. | 16022 |
| 37551435 | 16145 | .................................................. | 16102 |
| 88900616 | 18618 | .................................................. | 18575 |
| 88900616 | 18698 | .................................................. | 18655 |
| 88900616 | 185511 | .................................................. | 185554 |
| 88900616 | 185591 | .................................................. | 185634 |
| 44971363 | 17722 | .................................................. | 17679 |
| 44971363 | 17802 | .................................................. | 17759 |
| 47088326 | 10008 | .................................................. | 9965 |
| 47088326 | 10088 | .................................................. | 10045 |
| 56713341 | 15689 | .................................................. | 15646 |
| 56713341 | 15769 | .................................................. | 15726 |
| 56713625 | 15689 | .................................................. | 15646 |
| 56713625 | 15769 | .................................................. | 15726 |
| 56713624 | 15612 | .................................................. | 15569 |
| 56713624 | 15692 | .................................................. | 15649 |
| 18482913 | 15989 | .................................................. | 15946 |
| 18482913 | 15911 | ...................................................T......... | 15869 |
| 22123748 | 22960 | .................................................. | 22917 |
| 22123748 | 22878 | .............................-G.................. | 22837 |
| 19717929 | 14304 | .................................................. | 14261 |
| 19717929 | 14226 | ...............................................T......... | 14184 |
| 2772662 | 15798 | .................................................. | 15755 |
| 2772662 | 15878 | .................................................. | 15835 |
| 29692106 | 13086 | .................................................. | ·13043 |
| 29692106 | 13166 | .................................................. | 13123 |

FIGURE 8D

| | | | |
|---|---|---|---|
| 5830555 | 6996 | ................................................ | 6953 |
| 5830555 | 7072 | ................................................ | 7029 |
| 885796 | 7223 | ................................................ | 7180 |
| 885796 | 7299 | ................................................ | 7256 |
| 885724 | 6996 | ................................................ | 6953 |
| 885724 | 7072 | ................................................ | 7029 |
| 885686 | 7012 | ................................................ | 6969 |
| 885686 | 7088 | ................................................ | 7045 |
| 456758 | 6964 | ................................................ | 6921 |
| 456758 | 7040 | ................................................ | 6997 |
| 6969640 | 12632 | ................................................ | 12589 |
| 6969640 | 12712 | ................................................ | 12669 |
| 623595 | 7664 | ................................................ | 7621 |
| 623595 | 7740 | ................................................ | 7697 |
| 335691 | 3950 | ................................................ | 3907 |
| 335691 | 4030 | ................................................ | 3987 |
| 335317 | 16234 | ................................................ | 16191 |
| 335317 | 16154 | ................................................ | 16119 |
| 325559026 | 27934 | ........................................A....... | 27891 |
| 325559026 | 27854 | ................................................ | 27813 |
| 325514012 | 27520 | ........................................C....... | 27477 |
| 325514012 | 27600 | ................................................ | 27559 |
| 325559238 | 28458 | ................................................ | 28418 |
| 325559238 | 28540 | ........................................A....... | 28500 |
| 30795158 | 29579 | ................................................ | 29539 |
| 30795158 | 29661 | ........................................A....... | 29621 |
| 325557737 | 28302 | ........................................C....... | 28260 |
| 325557737 | 28382 | ................................................ | 28343 |
| 68449479 | 15249 | ...............................C....... | 15206 |
| 68449479 | 15169 | ...................... | 15154 |
| 68449280 | 15746 | ...............................C....... | 15703 |
| 68449280 | 15666 | ...................... | 15651 |
| 68448677 | 15249 | ...............................C....... | 15206 |
| 68448677 | 15169 | ...................... | 15154 |
| 59858806 | 15322 | ...............................C....... | 15279 |
| 59858806 | 15242 | ...................... | 15227 |
| 58220470 | 14913 | ...............................C....... | 14870 |
| 58220470 | 14833 | ...................... | 14818 |
| 51342166 | 15076 | ...............................C....... | 15033 |
| 51342166 | 14996 | ...................... | 14981 |
| 30519405 | 29201 | ...............................C....... | 29159 |
| 30519405 | 29282 | ...................... | 29243 |
| 323098609 | 13319 | ................................................ | 13289 |
| 323098609 | 13398 | ...............................-....... | 13356 |
| 323098410 | 13348 | ................................................ | 13318 |
| 323098410 | 13427 | ...............................-....... | 13385 |
| 300872625 | 13482 | ................................................ | 13452 |
| 300872625 | 13561 | ...............................-....... | 13519 |
| 56236951 | 7856 | ................................................ | 7826 |
| 56236951 | 7935 | ...............................-....... | 7893 |
| 68449077 | 13480 | ................................................ | 13450 |
| 68449077 | 13559 | ...............................-....... | 13517 |

| | |
|---|---|
| gi\|383866716\|JQ410350.1 | Ectromelia virus culture-collection ATCC:VR-1431, complete genome |
| gi\|373449558\|JN654986.1 | Vaccinia virus strain Dryvax clone DPP21, complete genome |
| gi\|373449318\|JN654985.1 | Vaccinia virus strain Dryvax clone DPP20, complete genome |
| gi\|373449076\|JN654984.1 | Vaccinia virus strain Dryvax clone DPP19, complete genome |
| gi\|373448847\|JN654983.1 | Vaccinia virus strain Dryvax clone DPP17, complete genome |
| gi\|373448604\|JN654982.1 | Vaccinia virus strain Dryvax clone DPP16, complete genome |
| gi\|373448367\|JN654981.1 | Vaccinia virus strain Dryvax clone DPP15, complete genome |
| gi\|373448133\|JN654980.1 | Vaccinia virus strain Dryvax clone DPP13, complete genome |
| gi\|373447891\|JN654979.1 | Vaccinia virus strain Dryvax clone DPP12, complete genome |
| gi\|373447653\|JN654978.1 | Vaccinia virus strain Dryvax clone DPP11, complete genome |
| gi\|373447414\|JN654977.1 | Vaccinia virus strain Dryvax clone DPP10, complete genome |
| gi\|373447175\|JN654976.1 | Vaccinia virus strain Dryvax clone DPP9, complete genome |
| gi\|325558812\|HQ420898.1 | Cowpox virus strain Germany_2002_MKY, complete genome |
| gi\|325558595\|HQ420897.1 | Cowpox virus strain Germany_1998_2, complete genome |
| gi\|325558381\|HQ420896.1 | Cowpox virus strain Germany_1990_2, complete genome |
| gi\|325558165\|HQ420895.1 | Cowpox virus strain Germany_1980_EP4, complete genome |
| gi\|325557951\|HQ420894.1 | Cowpox virus strain France_2001_Nancy, complete genome |
| gi\|167412463\|EU410304.1 | Vaccinia virus GLV-1h68, complete genome |
| gi\|160857876\|AM501482.1 | Vaccinia virus Ankara strain chorioallantois vaccinia virus Ankara (CVA), complete coding genome |
| gi\|149786253\|EF675191.1 | Vaccinia virus strain MVATGN33.1 Modified Virus Ankara, complete genome |
| gi\|119352440\|DQ121394.1 | Vaccinia virus strain Lister clone VACV107, complete genome |
| gi\|90819652\|DQ439815.1 | Vaccinia virus strain DUKE, complete genome |
| gi\|115607420\|DQ983239.1 | Vaccinia virus strain AGR-MVA-572pre genomic sequence |
| gi\|115607419\|DQ983238.1 | Vaccinia virus strain MVA-BN genomic sequence |
| gi\|115607418\|DQ983237.1 | Vaccinia virus strain MVA-572 genomic sequence |
| gi\|115607417\|DQ983236.1 | Vaccinia virus strain MVA-1721 genomic sequence |
| gi\|111184167\|DQ792504.1 | Horsepox virus isolate MNR-76, complete genome |
| gi\|109726482\|DQ437592.1 | Variola virus strain Syria 1972 V72-199, complete genome |
| gi\|109726279\|DQ437591.1 | Variola virus strain Sumatra 1970 V70-222, complete genome |
| gi\|109726076\|DQ437590.1 | Variola virus strain Somalia 1977, complete genome |
| gi\|109725872\|DQ437589.1 | Variola virus strain Pakistan 1969 (Rafig Lahore), complete sequence |
| gi\|109725669\|DQ437588.1 | Variola virus strain Nepal 1973, complete genome |
| gi\|109725465\|DQ437587.1 | Variola virus strain Iran 1972 2602 Tabriz, complete genome |
| gi\|109725262\|DQ437586.1 | Variola virus strain India 1964 7125 Vellore, complete genome |

FIGURE 9A

| | |
|---|---|
| gi\|109725056\|DQ437585.1 | Variola virus strain India 1964 7124 Vellore, complete genome |
| gi\|109724854\|DQ437584.1 | Variola virus strain Germany 1958 Heidelberg, complete genome |
| gi\|109724650\|DQ437583.1 | Variola virus strain Congo 1970, complete genome |
| gi\|109724445\|DQ437582.1 | Variola virus strain China Horn 1948, complete genome |
| gi\|109724243\|DQ437581.1 | Variola virus strain Bangladesh 1975 v75-550 Banu, complete genome |
| gi\|109724039\|DQ437580.1 | Variola virus strain Afghanistan 1970 Variolator 4, complete genome |
| gi\|94490104\|DQ441448.1 | Variola virus strain Yugoslavia 1972 V72-164, complete genome |
| gi\|94489896\|DQ441447.1 | Variola virus strain United Kingdom 1952 Butler, complete genome |
| gi\|94489695\|DQ441446.1 | Variola virus strain United Kingdom 1947 Higgins (Staffordshire), complete genome |
| gi\|94489496\|DQ441445.1 | Variola virus strain United Kingdom 1946 Hinden (Middlesex), complete genome |
| gi\|94489293\|DQ441444.1 | Variola virus strain United Kingdom 1946 Harvey, complete genome |
| gi\|94489094\|DQ441443.1 | Variola virus strain Tanzania 1965 kembula, complete genome |
| gi\|94488894\|DQ441442.1 | Variola virus strain Sumatra 1970 V70-228, complete genome |
| gi\|94488693\|DQ441441.1 | Variola virus strain Sudan 1947 (Rumbec), complete genome |
| gi\|94488492\|DQ441440.1 | Variola virus strain Sudan 1947 (Juba), complete genome |
| gi\|94488292\|DQ441439.1 | Variola virus strain Somalia 1977 (V77-1605), complete genome |
| gi\|94488092\|DQ441438.1 | Variola virus strain Somalia 1977 (V77-1252), complete genome |
| gi\|94487887\|DQ441437.1 | Variola virus strain Sierra Leone 1969 (V68-258), complete genome |
| gi\|94487685\|DQ441436.1 | Variola virus strain South Africa 1965 (103 T'vaal, Nelspruit), complete genome |
| gi\|94487484\|DQ441435.1 | Variola virus strain South Africa 1965 (102 Natal, Ingwavuma), complete genome |
| gi\|94487278\|DQ441434.1 | Variola virus strain Niger 1969 (001, importation from Nigeria), complete genome |
| gi\|94487078\|DQ441433.1 | Variola virus strain Kuwait 1967 (K1629), complete genome |
| gi\|94486875\|DQ441432.1 | Variola virus strain Korea 1947 (Lee, Masterseed), complete genome |
| gi\|94486673\|DQ441431.1 | Variola virus strain Japan 1951 (Stillwell, Masterseed), complete genome |
| gi\|94486471\|DQ441430.1 | Variola virus strain Japan 1951 (Harper, Masterseed), complete genome |
| gi\|94486268\|DQ441429.1 | Variola virus strain Japan 1946 (Yamada MS-2(A) Tokyo), complete genome |
| gi\|94486065\|DQ441428.1 | Variola virus strain India 1953 (New Delhi), complete genome |
| gi\|94485863\|DQ441427.1 | Variola virus strain India 1953 (Kali-Muthu-M50 Madras), complete genome |

FIGURE 9B

| | |
|---|---|
| gi\|94485659\|DQ441426.1 | Variola virus strain Guinea 1969 (005), complete genome |
| gi\|94485457\|DQ441425.1 | Variola virus strain Ethiopia 1972 (Eth17 R14-1X-72 Addis), complete genome |
| gi\|94485254\|DQ441424.1 | Variola virus strain Ethiopia 1972 (Eth16 R14-1X-72 Addis), complete genome |
| gi\|94485053\|DQ441423.1 | Variola virus strain Congo 9 1970 (v74-227 Gispen), complete genome |
| gi\|94484855\|DQ441422.1 | Variola virus strain Bangladesh 1974 (Solaiman), complete genome |
| gi\|94484657\|DQ441421.1 | Variola virus strain Bangladesh 1974 (Shahzaman), complete genome |
| gi\|94484460\|DQ441420.1 | Variola virus strain Bangladesh 1974 (nur islam), complete genome |
| gi\|94484252\|DQ441419.1 | Variola virus strain Brazil 1966 (v66-39 Sao Paulo), complete genome |
| gi\|94484050\|DQ441418.1 | Variola virus strain Botswana 1973 (v73-225), complete genome |
| gi\|94483847\|DQ441417.1 | Variola virus strain Botswana 1972 (v72-143), complete genome |
| gi\|94483641\|DQ441416.1 | Variola virus strain Benin, Dahomey 1968 (v68-59), complete genome |
| gi\|90660453\|DQ437594.1 | Taterapox virus strain Dahomey 1968, complete genome |
| gi\|90660233\|DQ437593.1 | Cowpox virus strain Germany 91-3, complete genome |
| gi\|38348858\|AY313847.1 | Vaccinia virus strain Acambis clone 2000, complete genome |
| gi\|37551435\|AY313848.1 | Vaccinia virus strain Acambis clone 3, complete genome |
| gi\|88900616\|DQ377945.1 | Vaccinia virus strain 3737, complete genome |
| gi\|44971363\|AY484669.1 | Rabbitpox virus, complete genome |
| gi\|47088326\|AY603355.1 | Vaccinia virus strain Acambis 3000 Modified Virus Ankara (MVA), complete genome |
| gi\|56713341\|AY678275.1 | Vaccinia virus strain LC16m8, complete genome |
| gi\|56713625\|AY678277.1 | Vaccinia virus strain LC16mO, complete genome |
| gi\|56713624\|AY678276.1 | Vaccinia virus strain Lister, complete genome |
| gi\|18482913\|AF438165.1 | Camelpox virus M-96 from Kazakhstan, complete genome |
| gi\|22123748\|AF012825.2 | Ectromelia virus strain Moscow, complete genome |
| gi\|19717929\|AY009089.1 | Camelpox virus CMS, complete genome |
| gi\|2772662\|U94848.1 | Vaccinia virus strain Ankara, complete genomic sequence |
| gi\|29692106\|AY243312.1 | Vaccinia virus WR, complete genome |
| gi\|5830555\|Y16780.1 | variola minor virus complete genome |
| gi\|885796\|U18340.1 | Variola virus Somalia-1977 left variable region |
| gi\|885724\|U18338.1 | Variola virus Garcia-1966 left near-terminal region |
| gi\|885686\|U18337.1 | Variola virus Congo-1965 left near-terminal region |
| gi\|456758\|X69198.1 | Variola virus DNA complete genome |
| gi\|6969640\|AF095689.1 | Vaccinia virus (strain Tian Tan) complete genome |
| gi\|623595\|L22579.1 | Variola major virus (strain Bangladesh-1975) complete genome |

FIGURE 9C

| | |
|---|---|
| gi\|335691\|M22812.1 | Vaccinia virus genome, left end |
| gi\|335317\|M35027.1 | Vaccinia virus Copenhagen, complete genome |
| gi\|325559026\|HQ420899.1 | Cowpox virus strain Norway_1994_MAN, complete genome |
| gi\|325514012\|HQ407377.1 | Cowpox virus strain Austria 1999, complete genome |
| gi\|325559238\|HQ420900.1 | Cowpox virus strain UK2000_K2984, complete genome |
| gi\|30795158\|AF482758.2 | Cowpox virus strain Brighton Red, complete genome |
| gi\|325557737\|HQ420893.1 | Cowpox virus strain Finland_2000_MAN, complete genome |
| gi\|68449479\|DQ011157.1 | Monkeypox virus strain USA_2003_039, complete genome |
| gi\|68449280\|DQ011156.1 | Monkeypox virus strain Liberia_1970_184, complete genome |
| gi\|68448677\|DQ011153.1 | Monkeypox virus strain USA_2003_044, complete genome |
| gi\|59858806\|AY753185.1 | Monkeypox virus strain COP-58, complete genome |
| gi\|58220470\|AY741551.1 | Monkeypox virus isolate Sierra Leone, complete genome |
| gi\|51342166\|AY603973.1 | Monkeypox virus strain MPXV-WRAIR7-61, complete genome |
| gi\|30519405\|X94355.2 | Cowpox virus strain GRI-90, complete genome |
| gi\|323098609\|HQ857563.1 | Monkeypox virus strain D14L knockout, complete genome |
| gi\|323098410\|HQ857562.1 | Monkeypox virus strain V79-I-005, complete genome |
| gi\|300872625\|HM172544.1 | Monkeypox virus strain Zaire 1979-005, complete genome |
| gi\|56236951\|AY743598.1 | Monkeypox virus strain Congo-8, partial |
| gi\|68449077\|DQ011155.1 | Monkeypox virus strain Zaire_1979-005, complete genome |
| gi\|68448876\|DQ011154.1 | Monkeypox virus strain Congo_2003_358, complete genome |
| gi\|17529780\|AF380138.1 | Monkeypox virus strain Zaire-96-I-16, complete genome |

FIGURE 9D

PR13.5 PROMOTER FOR ROBUST T-CELL AND ANTIBODY RESPONSES

This application is a National Phase application under 35 U.S.C. §371 of International Application No. PCT/EP2013/003239, filed Oct. 28, 2013, and claims the benefit under 35 U.S.C. §119(e) of US Provisional Patent Application 61/719,429 filed Oct. 28, 2012, the disclosures of which are incorporated by reference herein in their entirety.

This application is a National Phase application under 35 U.S.C. §371of International Application No. PCT/EP2013/003239, filed Oct. 28, 2013, and claims the benefit under 35 U.S.C. §119(e) of US Provisional Patent Application 61/719,429 filed Oct. 28, 2012, the disclosures of which are incorporated by reference herein in their entirety.

BACKGROUND OF THE INVENTION

MVA originates from the dermal vaccinia strain Ankara (Chorioallantois vaccinia Ankara (CVA) virus) that was maintained in the Vaccination Institute, Ankara, Turkey for many years and used as the basis for vaccination of humans. However, due to the often severe post-vaccinal complications associated with vaccinia viruses (VACV), there were several attempts to generate a more attenuated, safer smallpox vaccine.

During the period of 1960 to 1974, Prof. Anton Mayr succeeded in attenuating CVA by over 570 continuous passages in CEF cells (Mayr et al., 1975, Passage History: Abstammung, Eigenschaften and Verwendung des attenuierten Vaccinia-Stammes MVA. Infection 3: 6-14). As part of the early development of MVA as a pre-smallpox vaccine, there were clinical trials using MVA-517 (corresponding to the 517th passage) in combination with Lister Elstree (Stickl, 1974, Smallpox vaccination and its consequences: first experiences with the highly attenuated smallpox vaccine "MVA". Prev. Med. 3(1): 97-101; Stickl and Hochstein-Mintzel, 1971, Intracutaneous smallpox vaccination with a weak pathogenic vaccinia virus ("MVA virus"). Munch Med Wochenschr. 113: 1149-1153) in subjects at risk for adverse reactions from vaccinia. In 1976, MVA derived from MVA-571 seed stock (corresponding to the 571st passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with conventional vaccinia virus (Mayr et al., 1978, The smallpox vaccination strain MVA: marker, genetic structure, experience gained with the parenteral vaccination and behaviour in organisms with a debilitated defence mechanism (author's transl). Zentralbl. Bacteriol. (B) 167: 375-390). MVA-572 was deposited at the European Collection of Animal Cell Cultures, Vaccine Research and Production Laboratory, Public Health Laboratory Service, Centre for Applied Microbiology and Research, Porton Down, Salisbury, Wiltshire SP4 0JG, United Kingdom, as ECACC V9401 2707.

Being that many passages were used to attenuate MVA, there are a number of different strains or isolates, depending on the passage number in CEF cells. All MVA strains originate from Dr. Mayr and most are derived from MVA-572 that was used in Germany during the smallpox eradication program, or MVA-575 that was extensively used as a veterinary vaccine. MVA-575 was deposited on Dec. 7, 2000, at the European Collection of Animal Cell Cultures (ECACC) with the deposition number V001 20707.

By serial propagation (more than 570 passages) of the CVA on primary chicken embryo fibroblasts, the attenuated CVA-virus MVA (modified vaccinia virus Ankara) was obtained. MVA was further passaged by Bavarian Nordic and is designated MVA-BN. MVA, as well as MVA-BN, lacks approximately 13% (26.5 kb from six major and multiple minor deletion sites) of the genome compared with ancestral CVA virus. The deletions affect a number of virulence and host range genes, as well as a large fragment of the gene coding for A-type inclusion protein (ATI) and a gene coding for a structural protein directing mature virus particles into A-type inclusion bodies. A sample of MVA-BN was deposited on Aug. 30, 2000, at the European Collection of Cell Cultures (ECACC) under number V00083008.

MVA-BN can attach to and enter human cells where virally-encoded genes are expressed very efficiently. However, assembly and release of progeny virus does not occur. Preparations of MVA-BN and derivatives have been administered to many types of animals, and to more than 2000 human subjects, including immunodeficient individuals. All vaccinations have proven to be generally safe and well tolerated.

The perception from many different publications is that all MVA strains are the same and represent a highly attenuated, safe, live viral vector. However, preclinical tests have revealed that MVA-BN demonstrates superior attenuation and efficacy compared to other MVA strains (WO 02/42480). The MVA variant strains MVA-BN as, e.g., deposited at ECACC under number V00083008, have the capability of reproductive replication in vitro in chicken embryo fibroblasts (CEF), but no capability of reproductive replication in human cells in which MVA 575 or MVA 572 can reproductively replicate. For example, MVA-BN has no capability of reproductive replication in the human keratinocyte cell line HaCaT, the human embryo kidney cell line 293, the human bone osteosarcoma cell line 143B, and the human cervix adenocarcinoma cell line HeLa. Further, MVA-BN strains fail to replicate in a mouse model that is incapable of producing mature B and T cells, and as such is severely immune compromised and highly susceptible to a replicating virus. An additional or alternative property of MVA-BN strains is the ability to induce at least substantially the same level of immunity in vaccinia virus prime/vaccinia virus boost regimes when compared to DNA-prime/vaccinia virus boost regimes.

The term "not capable of reproductive replication" is used in the present application as defined in WO 02/42480 and U.S. Pat. No. 6,761,893, which are hereby incorporated by reference. Thus, the term applies to a virus that has a virus amplification ratio at 4 days after infection of less than 1 using the assays described in U.S. Pat. No. 6,761,893, which assays are hereby incorporated by reference. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells.

MVA-BN or its derivatives are, according to one embodiment, characterized by inducing at least substantially the same level of immunity in vaccinia virus prime/vaccinia virus boost regimes when compared to DNA-prime/vaccinia virus boost regimes. A vaccinia virus is regarded as inducing at least substantially the same level of immunity in vaccinia virus prime/vaccinia virus boost regimes when compared to DNA-prime/vaccinia virus boost regimes if the CTL response as measured in one of the "assay 1" and "assay 2" as disclosed in WO 02/42480, preferably in both assays, is at least substantially the same in vaccinia virus prime/vaccinia virus boost regimes when compared to DNA-prime/vaccinia virus boost regimes. More preferably, the CTL response after vaccinia virus prime/vaccinia virus boost administration is higher in at least one of the assays, when compared to DNA-prime/vaccinia virus boost regimes. Most preferably, the CTL response is higher in both assays.

WO 02/42480 discloses how vaccinia viruses are obtained having the properties of MVA-BN. The highly attenuated MVA-BN virus can be derived, e.g., by the further passage of a modified vaccinia virus Ankara (MVA), such as MVA-572 or MVA-575.

In summary, MVA-BN has been shown to have the highest attenuation profile compared to other MVA strains and is safe even in severely immunocompromised animals.

Although MVA exhibits strongly attenuated replication in mammalian cells, its genes are efficiently transcribed, with the block in viral replication being at the level of virus assembly and egress. (Sutter and Moss, 1992, Nonreplicating vaccinia vector efficiently expresses recombinant genes. Proc. Natl. Acad. Sci. U.S.A. 89: 10847-10851; Carroll and Moss, 1997, Host range and cytopathogenicity of the highly attenuated MVA strain of vaccinia virus: propagation and generation of recombinant viruses in a nonhuman mammalian cell line. Virology 238: 198-211.) Despite its high attenuation and reduced virulence, in preclinical studies MVA-BN has been shown to elicit both humoral and cellular immune responses to VACV and to the products of heterologous genes cloned into the MVA genome (Harrer et al., 2005, Therapeutic Vaccination of HIV-1-infected patients on HAART with recombinant HIV-1 nef-expressing MVA: safety, immunogenicity and influence on viral load during treatment interruption. Antiviral Therapy 10: 285-300; Cosma et al., 2003, Therapeutic vaccination with MVA-HIV-1 nef elicits Nef-specific T-helper cell responses in chronically HIV-1 infected individuals. Vaccine 22(1): 21-29; Di Nicola et al., 2003, Clinical protocol. Immunization of patients with malignant melanoma with autologous CD34(+) cell-derived dendritic cells transduced ex vivo with a recombinant replication-deficient vaccinia vector encoding the human tyrosinase gene: a phase I trial. Hum Gene Ther. 14(14): 1347-1 360; Di Nicola et al., 2004, Boosting T cell-mediated immunity to tyrosinase by vaccinia virus-transduced, CD34(+)-derived dendritic cell vaccination: a phase I trial in metastatic melanoma. Clin Cancer Res. 10(16): 5381-5390.)

MVA-BN and recombinant MVA-BN-based vaccines can be generated, passaged, produced and manufactured in CEF cells cultured in serum-free medium. Many recombinant MVA-BN variants have been characterized for preclinical and clinical development. No differences in terms of the attenuation (lack of replication in human cell lines) or safety (preclinical toxicity or clinical studies) have been observed between MVA-BN, the viral vector backbone, and the various recombinant MVA-based vaccines.

Induction of a strong humoral and cellular immune response against a foreign gene product expressed by a VACV vector is hampered by the fact that the foreign gene product has to compete with all of the more than 150 antigens of the VACV vector for recognition and induction of specific antibodies and T cells. The specific problem is the immunodominance of vector CD8 T cell epitopes which prevents induction of a strong CD8 T cell response against the foreign gene product. (Smith et al., Immunodominance of poxviral-specific CTL in a human trial of recombinant-modified vaccinia Ankara. J. Immunol. 175:8431-8437, 2005.) This applies to replicating VACV vectors such as Dryvax, as well as for non-replicating vectors like NYVAC and MVA.

For expression of a recombinant antigen ("neoantigen") by VACV, only poxvirus-specific promoters, but not common eukaryotic promoters, can be used. The reason for this is the specific biology of poxviruses which replicate in the cytoplasm and bring their own, cell-autonomous transcriptional machinery with them that does not recognize typical eukaryotic promoters.

The viral replication cycle is divided into two major phases, an early phase comprising the first two hours after infection before DNA replication, and a late phase starting at the onset of viral DNA replication at 2-4 hours after infection.

The late phase spans the rest of the viral replication cycle from ~2-20 h after infection until progeny virus is released from the infected cell. There are a number of poxviral promoter types which are distinguished and named by the time periods within the viral replication cycle in which they are active, for example, early and late promoters. (See, e.g., Davison and Moss, J. Mol. Biol. 210:771-784, 1989; Davison and Moss, J. Mol. Biol. 210:749-769, 1989; and Hirschmann et al., Journal of Virology 64:6063-6069, 1990, all of which are hereby incorporated by reference.)

Whereas early promoters can also be active late in infection, activity of late promoters is confined to the late phase. A third class of promoters, named intermediate promoters, is active at the transition of early to late phase and is dependent on viral DNA replication. The latter also applies to late promoters, however, transcription from intermediate promoters starts earlier than from typical late promoters and requires a different set of transcription factors.

It became increasingly clear over recent years that the choice of the temporal class of poxviral promoter for neoantigen expression has profound effects on the strength and quality of the neoantigen-specific immune response. It was shown that T cell responses against neoantigens expressed under the control of a late promoter are weaker than those obtained with the same antigen under an early promoter. (Bronte et al., Antigen expression by dendritic cells correlates with the therapeutic effectiveness of a model recombinant poxvirus tumor vaccine. Proc. Natl. Acad. Sci. U.S.A 94:3183-3188, 1997. Coupar et al., Temporal regulation of influenza hemagglutinin expression in vaccinia virus recombinants and effects on the immune response. Eur. J. Immunol. 16:1479-1487, 1986.)

Even more strikingly, it was recently shown that in repeated autologous immunizations with VACV as well as with the replication-defective VACV vector MVA, CD8 T cell responses against antigens under an exclusively late promoter can fail completely. This failure resulted in an almost undetectable antigen-specific CD8 T cell response after the second immunization. (Kastenmuller et al., Cross-competition of CD8+ T cells shapes the immunodominance hierarchy during boost vaccination. J. Exp. Med. 204:2187-2198, 2007.)

Thus, early expression of neoantigens by VACV vectors appears to be crucial for efficient neoantigen-specific CD8 T cell responses. It has also been shown that an early-expressed VACV vector antigen not only competes with late expressed antigens but also with other early antigens for immunodominance in the CD8 T cell response. (Kastenmuller et al., 2007.) The specific properties of the early portion of the poxviral promoter might thus be very important for induction of a neoantigen-specific T cell response. Moreover, it is a commonly held view and a general rule that higher amounts of antigen are beneficial for induction of stronger antigen-specific immune responses (for the poxvirus field, see for example Wyatt et al., Correlation of immunogenicities and in vitro expression levels of recombinant modified vaccinia virus Ankara HIV vaccines. Vaccine 26:486-493, 2008).

A promoter combining 4 early promoter elements and a late promoter element from the ATI gene has been described previously (Funahashi et al., Increased expression in vivo and in vitro of foreign genes directed by A-type inclusion body hybrid promoters in recombinant vaccinia viruses. J. Virol. 65:5584-5588, 1991; Wyatt et al., Correlation of immunogenicities and in vitro expression levels of recombinant modified vaccinia virus Ankara HIV vaccines. Vaccine 26:486-493, 2008), and has been shown to direct increased early expression of antigen. However, T cell responses induced by an antigen driven by such a promoter have only been analyzed after a single immunization and were not apparently different from those obtained with the classical Pr7.5K promoter in this setting. (Funahashi et al., Increased expression in vivo and in vitro of foreign genes directed by A-type inclusion body hybrid promoters in recombinant vaccinia viruses. J. Virol. 65:5584-5588, 1991.)

Jin et al. Arch. Virol. 138:315-330, 1994, reported the construction of recombinant VACV promoters consisting of a VACV ATI promoter combined with tandem repeats (2 to 38 copies) of a mutated Pr7.5 promoter operably linked to the CAT gene. Up to 10 repetitions of the mutated Pr7.5 promoter were effective in increasing early gene expression. Further repetition appeared to be inhibitory. With all constructs, the amount of CAT protein produced in the presence of cytosine arabinoside (AraC) (i.e. when the viral replication cycle was arrested in the early phase) was less than one-tenth of the amount produced in the absence of AraC (Jin et al. Arch. Virol. 138:315-330, 1994).

Recently, it was shown that repeated immunizations of mice with recombinant MVA expressing OVA under the control of a hybrid early-late promoter (pHyb) containing five copies of a strong early element led to superior acute and memory CD8 T-cell responses compared to those to Pr7.5- and PrS-driven OVA. Baur et al., Journal of Virology, Vol. 84 (17): 8743-8752 (2010). Moreover, OVA expressed under the control of pHyb replaced the MVA-derived B8R protein as the immunodominant CD8 T-cell antigen after three or more immunizations. Id.

Assarsson et al., P.N.A.S. 105: 2140-45, 2008, simultaneously measured the expression levels of 223 annotated vaccinia virus genes during infection and determined their kinetics using a genome tiling array approach. They found that many genes in the WR strain of Vaccinia virus had high transcription rates. Assarsson et al. provided some examples of highly expressed genes: immediate-early, VACWR-059 (double-stranded RNA-binding protein) and VACWR-184 (unknown); early, VACWR-018 (unknown); early/late, VACWR-131 (core protein); and late, VACWR-169 (unknown). Assarsson et al. indicated that, because of their exceptionally high expression levels, these genes might be of special interest for future investigations, but did not identify the promoters initiating transcription of these genes.

Yang et al., P.N.A.S. 107:11513-11518, 2010, used deep RNA sequencing to analyze vaccinia virus (VACV) transcriptomes at progressive times following infection. Before viral DNA replication, transcripts from 118 VACV ORFs were detected; after replication, transcripts from 93 additional ORFs were characterized. The high resolution permitted determination of the precise boundaries of many mRNAs including read-through transcripts and location of mRNA start sites and adjacent promoters.

Orubu et al, PLoS ONE 7(6):e40167, 2012, showed that potent early promoters that drive expression of non-functional or non-essential MVA open reading frames (ORFs) can be harnessed for immunogenic expression of recombinant antigen. Precise replacement of the MVA orthologs of C11R, F11L, A44L and B8R with a model antigen positioned to use the same translation initiation codon allowed early transgene expression similar to or slightly greater than that achieved by the commonly-used p7.5 or short synthetic promoters. The frequency of antigen-specific CD8+ T cells induced in mice by single shot or adenovirus-prime, rMVA-boost vaccination were similarly equal or marginally enhanced using endogenous promoters at their authentic genomic loci compared to the traditional constructs. The enhancement in immunogenicity observed using the C11R or F11L promoters compared with p7.5 was similar to that obtained with the mH5 promoter compared with p7.5.

Strong T cell and antibody responses against antigens encoded by recombinant poxviruses can improve vaccine efficacy. Consequently, a need in the art exists for compositions and methods capable of achieving strong T cell and antibody responses against antigens encoded by recombinant poxviruses, such as MVA. The invention fulfills this need.

BRIEF SUMMARY OF THE INVENTION

The invention encompasses a recombinant modified Vaccinia Ankara (MVA) virus comprising a Pr13.5 promoter linked to a nucleotide sequence encoding a neoantigen and uses thereof. In one embodiment, the invention encompasses a method of inducing a robust CD8 T cell response against a neoantigen in mammal, preferably a human, comprising administering one or more immunizations of the MVA virus to the mammal, including a human.

In various embodiments, the Pr13.5 promoter comprises at least 1 copy of a nucleic acid sequence of at least 40 bases having at least 95%, 98%, or 100% identity with SEQ ID NO:1.

In various embodiments, the Pr13.5 promoter comprises at least 1 copy of a second nucleotide sequence of at least 31 nucleotides that has at least 95%, 98% or 100% identity with SEQ ID NO:1.

In various embodiments, the Pr13.5 promoter comprises 2 copies of a nucleotide sequence of at least 40 nucleotides that has 100% identity with SEQ ID NO:1.

In various embodiments, the Pr13.5 promoter comprises SEQ ID NO:2.

BRIEF DESCRIPTION OF THE DRAWINGS

FIG. 2 depicts the sequence and position of the Pr13.5-long and Pr13.5-short promoters in the MVA genome (SEQ ID NO:3). There is a 44 bp sequence repeat (direct repeat) in the upstream sequence of the MVA013.5 gene. Boxed: boxed is the 44 bp repeated sequence in the upstream sequence of 13.5, which is separated by a 36 bp spacer. Dashed line: Pr13.5-long (Pos. 15878-15755). Solid line: Pr13.5-short (Pos. 15808-15755). Underlined: ATG start codon of MVA013.5 (Pos. 15703-15701). Positions according to GenBank DQ983238.1.

FIGS. 7A and 7B depict antibody production from the indicated constructs after the first, second and third immunizations. A. Geometric mean titer (GMT) of antibodies. B. Ratio of GMT compared to PrS promoter. The promoters MVA50L+PrSSL and MVA170R+PrSSL are the MVA promoters of the respective genes fused at the 5' side of the synthetic Short Strong Late promoter PrSSL promoter directly upstream of the ATG of the ovalbumin gene. (AATTTTTAATATATAA; SEQ ID NO:7; PCT WO 2010/060632 A1.)

FIGS. 8A-8F depict a BLAST alignment of the nucleotide sequences of various poxvirus Pr13.5 promoters with SEQ ID NO:1. Identical nucleotides are depicted by dots, missing nucleotides are depicted by dashes, and changes are indicated by letters.

FIGS. 9A-9D depict accession numbers and names for the sequences in the alignments in FIGS. 8A-8F.

DETAILED DESCRIPTION OF THE INVENTION

HeLa cells were infected with MVA-BN and RNA was prepared. Primers specific for various MVA ORFs were generated and RACE-PCR (FirstChoice® RLM-RACE Kit, Life Technologies, Darmstadt, Germany) was used to generate PCR products representative of the MVA RNAs encoding these ORFs. The PCR products were sequenced to identify the transcription start sites. Based on this information, promoters were identified for the transcription of mRNAs encoding these ORFs. The MVA promoters for the following ORFs were inserted into MVA constructs to drive expression of the ovalbumin (OVA) gene: MVA13.5 (CVA022; WR 018), MVA050L (E3L; WR 059), MVA022L (K1L; WR 032), and MVA170R (B3R; WR 185).

HeLa cells were infected in vitro with the recombinant MVA viruses and ovalbumin protein expression was examined by FACS analysis. No ovalbumin protein expression was detected by FACS analysis for constructs containing the MVA050L (E3L; WR 059), MVA022L (K1L; WR 032), and MVA170R (B3R; WR 185) promoters at 2, or even 4, hours after infection. In contrast, high level ovalbumin expression was detected with the MVA13.5 (CVA022; WR 018) promoter already after 2 hours.

A putative promoter core element for the MVA13.5L ORF was previously identified in Yang et al., 2010, as containing a 15 nt core sequence, and an untranslated leader of 177 nt. However, the current study indicated that the transcriptional start sites used by MVA13.5L ORF were downstream of the start site identified by Yang et al. by more than 100 nucleotides. Consequently, the MVA13.5 promoter identified by the inventors differs from the promoter core element identified by Yang et al.

Figure 8F:
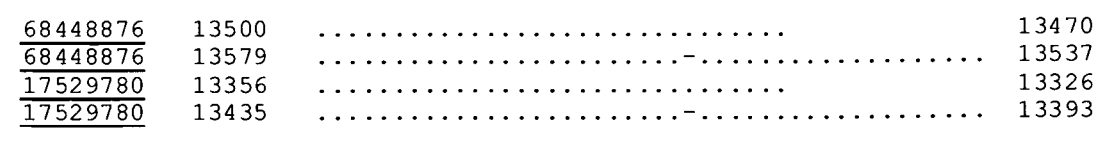

The MVA13.5 promoter identified by the inventors contains a repeat of over 40 nucleotides: TAAAAATAGAAAC-TATAATCATATAATAGTGTAGGTTGGTAGTA (SEQ ID NO:1). The repeated sequence can also be found in many other poxviruses, for example, horsepox virus, monkeypox virus, cowpox virus, variola virus, vaccinia virus, camelpox virus, rabbitpox virus, Ectromelia virus, and taterapox virus (FIGS. 8 and 9).

Figure 4:
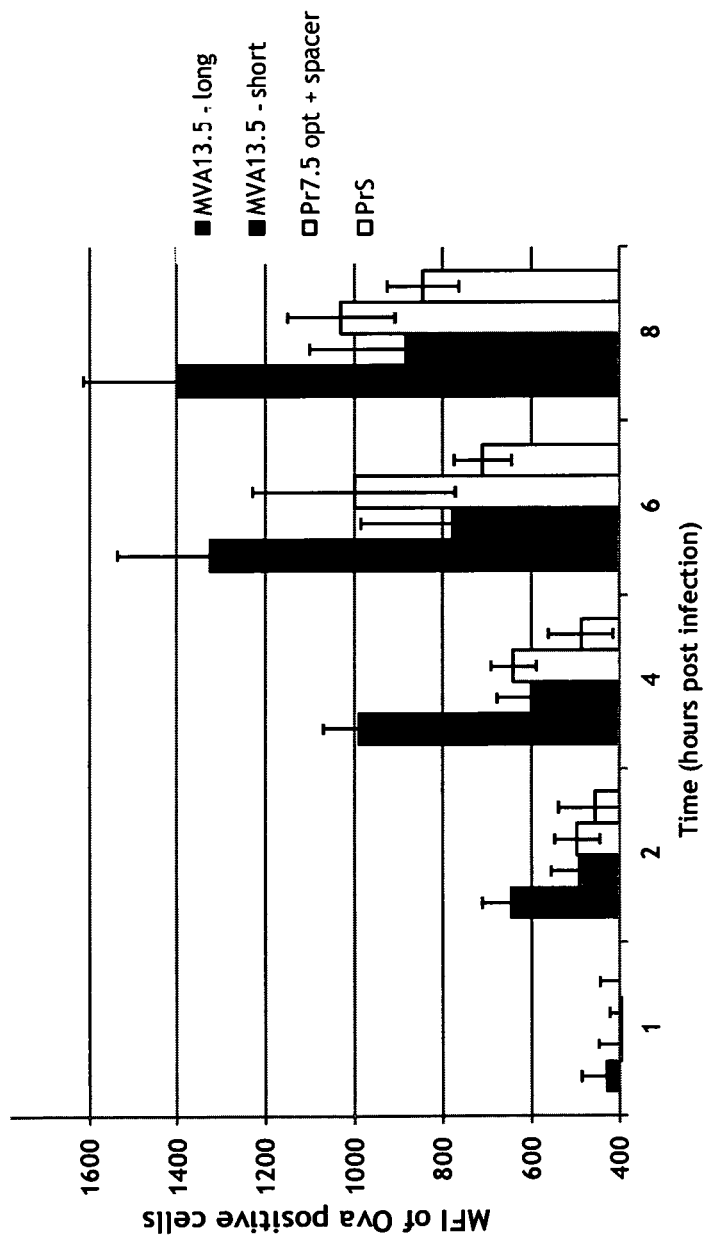
FIG. 4 depicts Ova protein expression measured by FACS as mean fluorescence intensity (MFI) from HeLa cells infected with the indicated constructs at the post infection time points indicated. The mean of the wt (no Ova gene included) at 399 MFI reflects the background of the assay.

Two MVA constructs were generated with promoters containing one copy (MVA13.5 short; SEQ ID NO:1) or two copies (MVA13.5 long; SEQ ID NO:2) of the repeat driving expression of the ovalbumin (OVA) gene. High level ovalbumin expression was detected after infection of HeLa cells in vitro with both of the constructs. (FIG. 4.)

Figure 1:
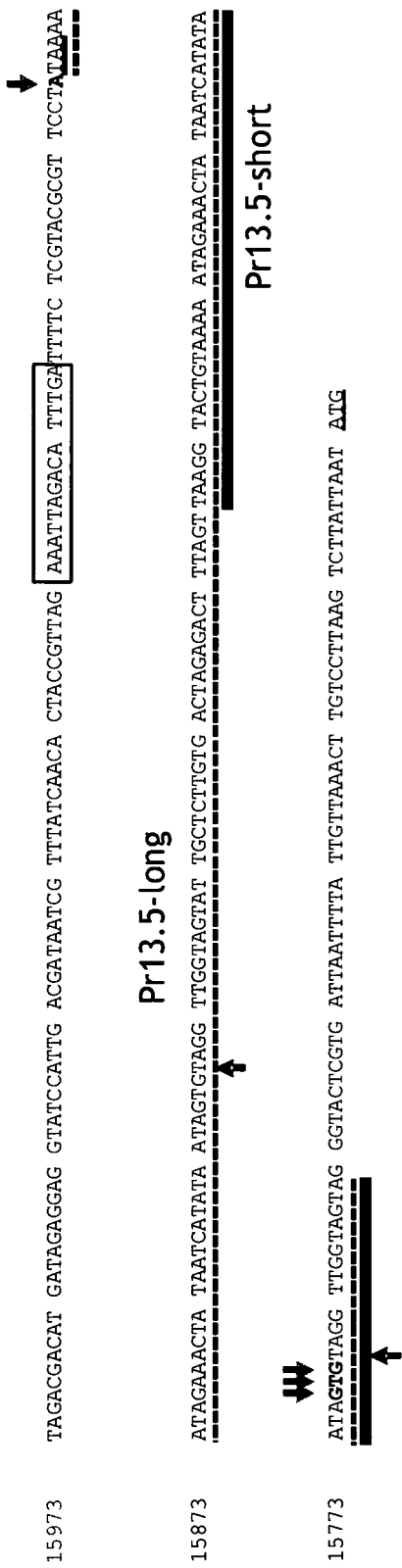
FIG. 1 depicts the upstream sequence of the MVA013.5L gene (SEQ ID NO:3). Sequences of the Pr13.5-short and Pr13.5-long promoters are given. Dashed line: Pr13.5-long (Pos. 15878-15755). Solid line: Pr13.5-short (Pos. 15808-15755). Underlined: ATG start codon of MVA013.5 (Pos. 15703-15701). TAA stop codon of MVA014L (Pos. 15878-15856). Black arrows from below: transcription start sites as defined by RACE PCR (Pos. 15767 and 15747). Grey arrows from top: transcription start sites as defined by Yang et al., 2010, suppl. data. Boxed: core promoter as defined by Yang et al., 2010, suppl. data (Pos. 15913-15899). Positions according to GenBank DQ983238.1
Figure 3:
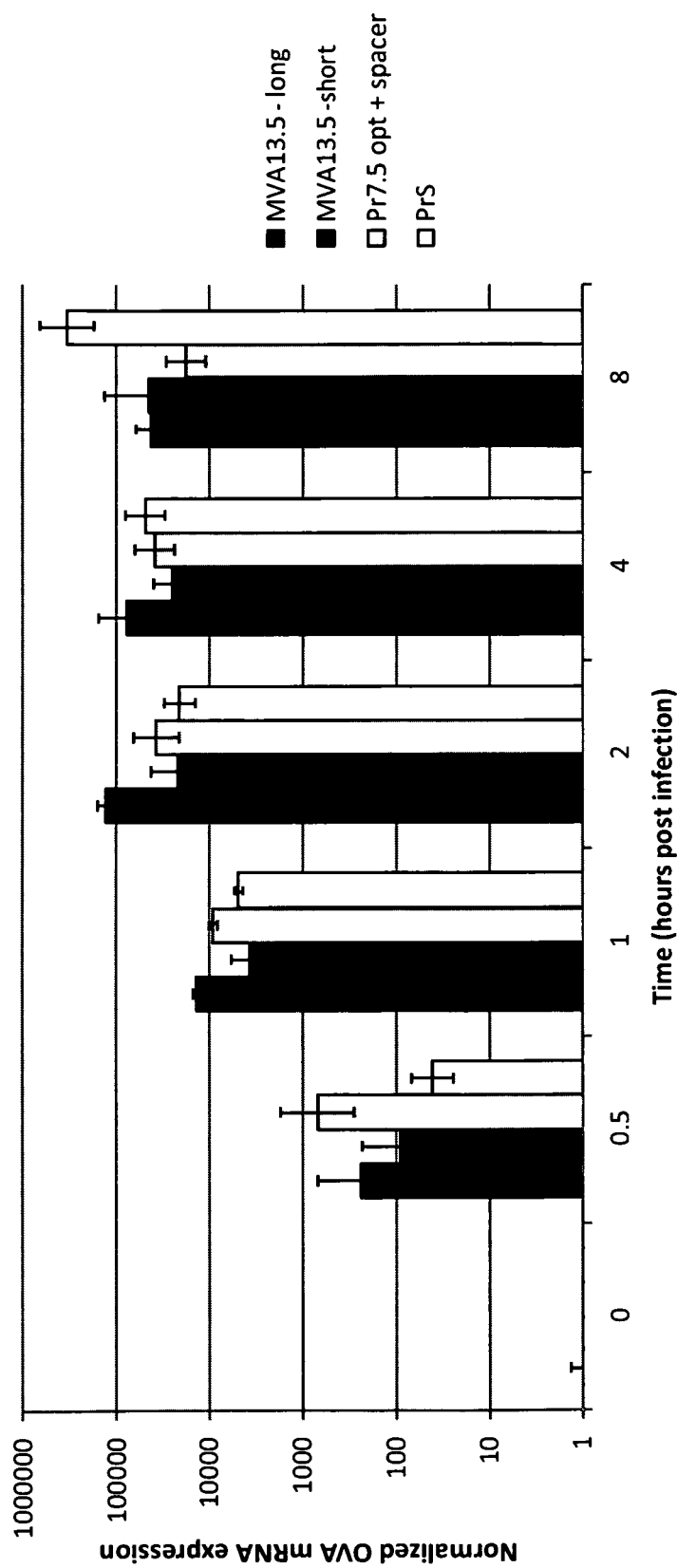
FIG. 3 depicts RT-qPCR measuring ovalbumin-mRNA from HeLa cells infected with the indicated constructs at the post infection time points indicated.

Ovalbumin RNA expression directed by various promoters in infected HeLa cells in vitro was measured at various time points by RT-qPCR. Both MVA13.5 short and MVA13.5 long showed high levels of early RNA expression. (FIG. 3.) MVA13.5 long showed the highest levels of early protein expression.

Figure 5:
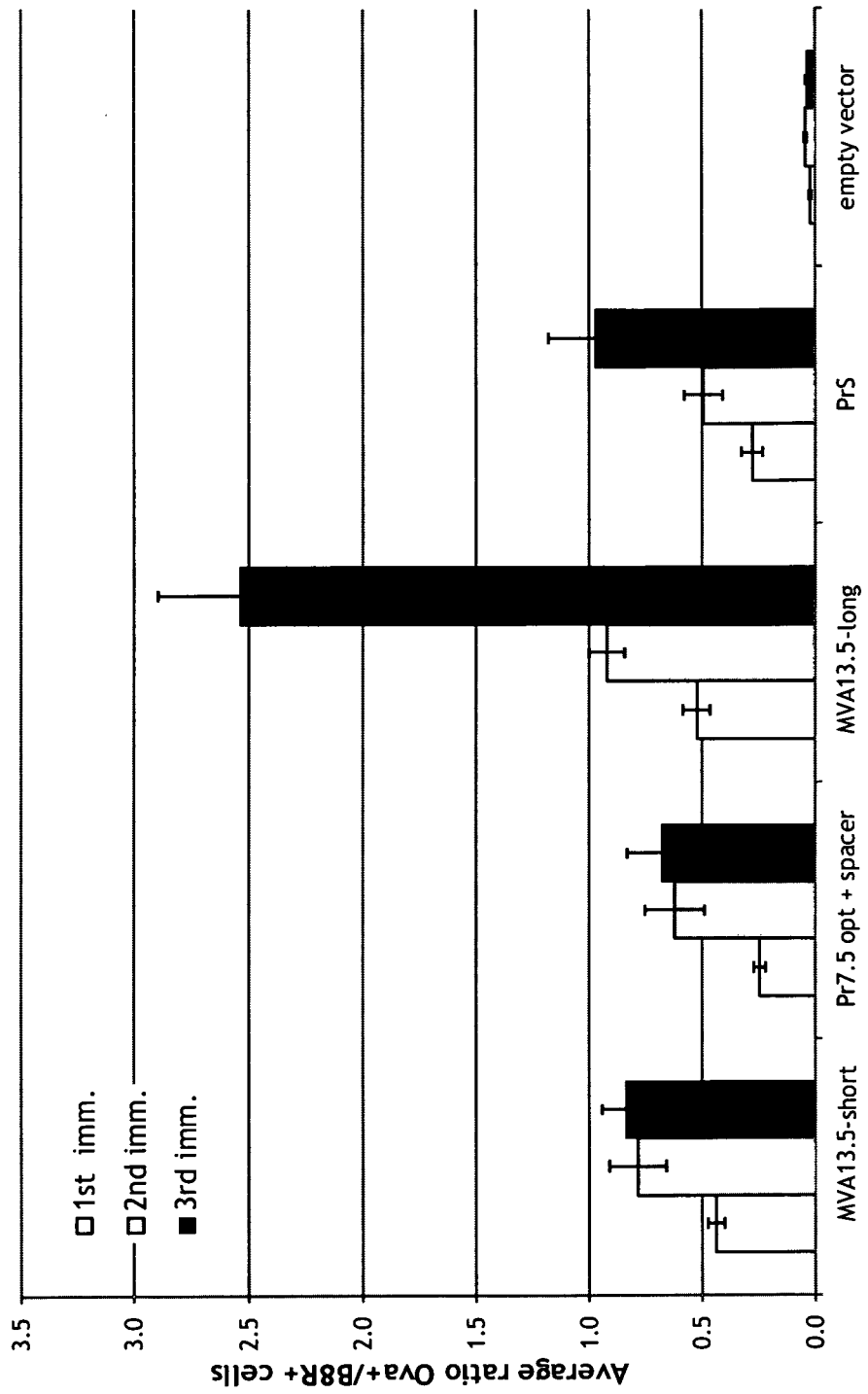
FIG. 5 depicts the average ratio of Ova+/B8R+ cells from mice vaccinated with the indicated constructs after the first, second and third immunizations.
Figure 6:
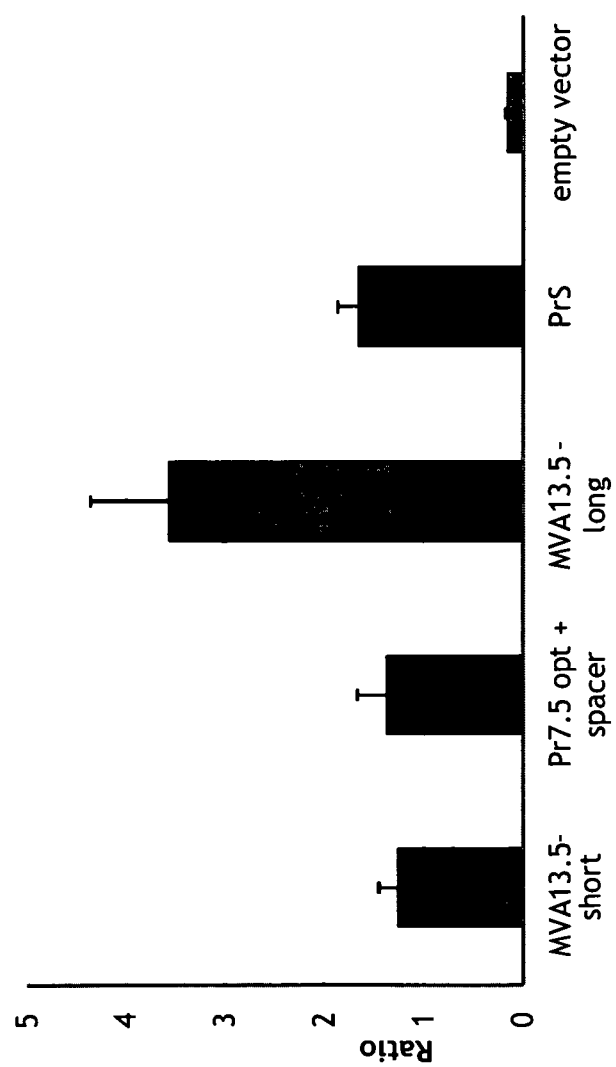
FIG. 6 depicts the average ratio of Ova+/B8R+T cell response of mice at 10 weeks after the third immunization with the indicated constructs.

CD8 T cell responses against recombinantly expressed OVA under control of the promoters PrS, Pr7.5 opt+spacer, Pr13.5 short and Pr13.5 long were determined in mice after one, two, and three immunizations of recombinant MVA per mouse (FIG. 5-6.). The OVA-specific and B8R(viral)-specific CD8 T cell response was determined by assessing the number of CD8 T cells specifically binding to MHC class I hexamers. The MHC class I dextramers were complexed with their respective H-2Kb binding peptides, SIINFEKL (SEQ ID NO:4) for OVA or TSYKFESV (SEQ ID NO:5) for the viral B8R peptide.

The average ratio of OVA-specific to B8R-specific CD8 T cells was approximately 2.5 for MVA13.5-long after 3 immunizations. The other 3 constructs showed an average ratio of less than 1. Thus, a reversal of the immunodominance hierarchy could be achieved by using the Pr13.5 long promoter for expression of the neoantigen, but not by using the other promoters.

Figure 7A:
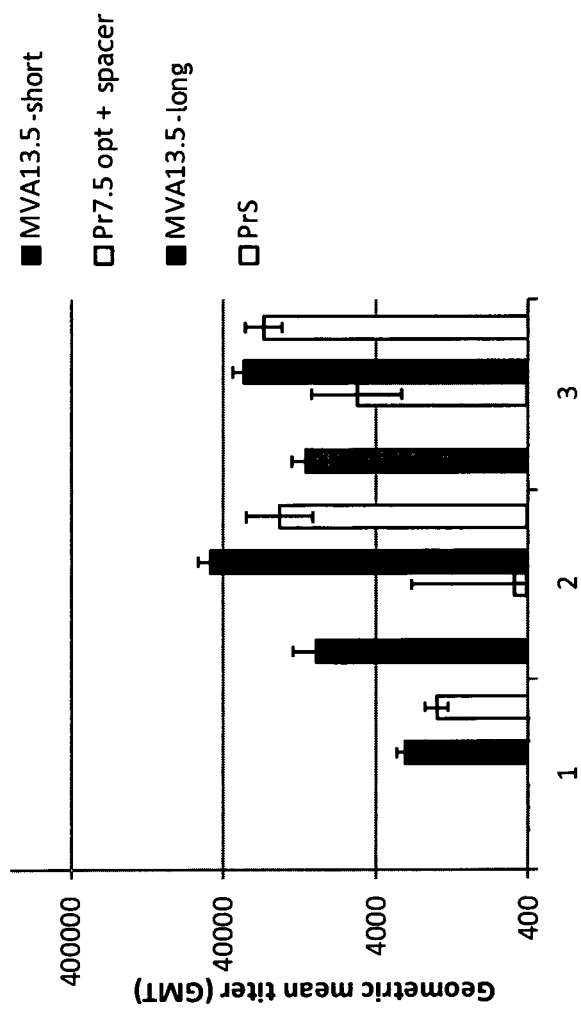

Antibody responses against recombinantly expressed OVA under control of various promoters were determined in mice after one, two, and three immunizations of recombinant MVA per mouse. (FIG. 7A-B.) The antibody response with MVA13.5 long was substantially higher than the response using a recombinant MVA with the PrS promoter. Thus, the use of the Pr13.5 long promoter to drive neoantigen expression from MVA provides unexpectedly superior results.

Pr13.5 Promoters

The invention encompasses isolated nucleic acids comprising or consisting of a Pr13.5 promoter. Within the context of this invention, a "Pr13.5 promoter" comprises at least 1 copy of a nucleic acid sequence of at least 40 bases having at least 95% identity with SEQ ID NO:1. Thus, a "Pr13.5 promoter" can, in various embodiments, refer to an MVA nucleotide sequence, a synthetic sequence, or an analogous poxviral sequence from a poxvirus other than MVA. Preferably, the Pr13.5 promoter comprises at least 1 copy of a nucleic acid sequence of at least 40 bases having at least 96%, 97%, 98%, 99%, or 100% identity with SEQ ID NO:1. The nucleic acid sequence is preferably 40, 41, 42, 43, 44, or 45 bases in length.

The percent identity can be determined by visual inspection and mathematical calculation. Alternatively, the percent identity of two nucleic acid sequences can be determined by comparing sequence information using the GAP computer program, version 6.0 described by Devereux et al. (Nucl. Acids Res. 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

Preferably, the Pr13.5 promoter is operably linked to a heterologous nucleic acid sequence. Within the context of this invention, "heterologous nucleic acid sequence" means a nucleic acid sequence to which the promoter is not linked in nature. Within the context of this invention, "operably linked" means that the promoter can drive expression of the heterologous nucleic acid sequence in a poxvirus infected cell. The heterologous nucleic acid sequence preferably encodes a neoantigen. Within the context of this invention, a neoantigen refers to an antigen not naturally expressed by the poxviral vector.

The Pr13.5 promoter can be operably linked to a heterologous nucleic acid sequence by recombinant DNA technology. In various embodiments, the heterologous nucleic acid sequence is introduced into the 13.5 ORF of the poxvirus.

Preferably, the Pr13.5 promoter is a naturally occurring poxvirus promoter. For example, the Pr13.5 promoter can be from modified vaccinia Ankara (MVA) virus, monkeypox virus, cowpox virus, variola virus, vaccinia virus, camelpox virus, rabbitpox virus, Ectromelia virus, or taterapox virus Pr13.5 promoter. Preferred Pr13.5 promoters can be selected from the viruses shown in FIG. 9 and the sequences shown in FIG. 8.

In various embodiments, the Pr13.5 promoter is a synthetic Pr13.5 promoter.

The Pr13.5 promoter can contain 1, 2, 3, 4, 5, 6, or more copies of a sequence of at least 40, 41, 42, 43, 44, or 45 nucleotides that has at least 95%, 96%, 97%, 98%, 99%, or 100% identity with SEQ ID NO:1.

Preferably, the Pr13.5 promoter contains 1 copy of the nucleotide sequence of SEQ ID NO:1.

In some embodiments, the Pr13.5 promoter contains 1 copy of the nucleotide sequence of SEQ ID NO:1 and 1, 2, 3, 4, 5, 6, or more copies of a sequence of at least 40, 41, 42, 43, or 44 nucleotides that has at least 95%, 96%, 97%, 98%, 99%, or 100% identity with SEQ ID NO:1.

Preferably, the Pr13.5 promoter contains at least 1 copy of a nucleotide sequence of at least 40 bases that has at least 98% identity with SEQ ID NO:1.

In some embodiments, the Pr13.5 promoter contains 1 copy of a nucleotide sequence of at least 40 bases that has at least 95%, 96%, 97%, 98%, 99%, or 100%% identity with SEQ ID NO:1 and 1, 2, 3, 4, 5, 6, or more copies of a second nucleotide sequence of at least 31 nucleotides that has at least 95%, 96%, 97%, 98%, 99%, or 100% identity with SEQ ID NO:1. Preferably the second nucleotide sequence is at least 31, 32, 33, 34, 35, 36, 37, 38, 39, 40, 41, 42, 43, 44, or 45 bases.

Preferably, the repeated sequences are separated by 20-80 nucleotides, more preferably 30-40 nucleotides, and most preferably of 33, 35, 35, 36, 37, 38, 39, or 40 nucleotides.

Preferably, the Pr13.5 promoter comprises at least one copy of the sequence:

```
                                           (SEQ ID NO: 2)
TAAAAATAGAAACTATAATCATATAATAGTGTAGGTTGGTAGTATTGCTC

TTGTGACTAGAGACTTTAGTTAGGTACTGTAAAAATAGAAACTATAATCA

TATAATAGTGTAGGTTGGTAGTA.
```

In some embodiments, the Pr13.5 promoter comprises one or more of the nucleotide changes shown in FIG. 8.

The invention encompasses methods of expressing a neoantigen comprising operably linking a Pr13.5 promoter to a heterologous nucleic acid sequence.

Recombinant Poxviruses Comprising Pr13.5 Promoters

The invention encompasses a recombinant poxviral vector comprising a Pr13.5 promoter operably linked to a heterologous nucleic acid sequence. In one embodiment, the heterologous nucleic acid sequence is inserted into the 13.5 ORF of a poxvirus so as to operably link the heterologous nucleic acid sequence to the endogenous viral Pr13.5 promoter. In another embodiment, the heterologous nucleic acid sequence is linked to a Pr13.5 promoter and inserted into a site in the genome other than the 13.5 ORF.

Preferably, the poxvirus vector is derived from poxviruses belonging to the Chordopoxvirinae subfamily. Poxviruses include those belonging to the genera Orthopoxvirus, Parapoxvirus, Avipoxvirus, Capripoxvirus, Lepripoxvirus, Suipoxvirus, Molluscipoxvirus and Yatapoxvirus. Most preferred are poxviruses belonging to the genera Orthopoxvirus and Avipoxvirus.

Other poxviruses such as racoonpox and mousepox may be employed in the present invention, for example, for the manufacture of wild-life vaccine. Members of the capripoxvirus and leporipox are also included herein as they may be useful as vectors for cattle and rabbits, respectively.

In other embodiments, the poxvirus is derived from avipoxviruses. Examples of avipoxviruses suitable for use in the present invention include any avipoxvirus such as fowlpoxvirus, canarypoxvirus, uncopoxvirus, mynahpoxvirus, pigeonpoxvirus, psittacinepoxvirus, quailpoxvirus, peacockpoxvirus, penguinpoxvirus, sparrowpoxvirus, starlingpoxvirus and turkeypoxvirus. Preferred avipoxviruses are canarypoxvirus and fowlpoxvirus.

Preferably, the poxvirus is a vaccinia virus, most preferably MVA. The invention encompasses recombinant MVA viruses generated with any and all MVA viruses. Preferred MVA viruses are MVA variant strains MVA-BN as, e.g., deposited at ECACC under number V00083008; MVA-575, deposited on Dec. 7, 2000, at the European Collection of Animal Cell Cultures (ECACC) with the deposition number V001 20707; and MVA-572, deposited at the European Collection of Animal Cell Cultures as ECACC V9401 2707. Derivatives of the deposited strain are also preferred.

Preferably, the MVA has the capability of reproductive replication in vitro in chicken embryo fibroblasts (CEF) or other avian cell lines or in vivo in embryonated eggs, but no capability of reproductive replication in human cells in which MVA 575 or MVA 572 can reproductively replicate. Most preferably, the MVA has no capability of reproductive replication in the human keratinocyte cell line HaCaT, the human embryo kidney cell line 293, the human bone osteosarcoma cell line 143B, and the human cervix adenocarcinoma cell line HeLa.

In preferred embodiments, the Modified vaccinia virus Ankara (MVA) virus is characterized by having the capability of reproductive replication in vitro in chicken embryo fibroblasts (CEF) and by being more attenuated than MVA-575 in the human keratinocyte cell line HaCaT, in the human bone osteosarcoma cell line 143B, and in the human cervix adenocarcinoma cell line HeLa. Preferably, the MVA virus is capable of a replication amplification ratio of greater than 500 in CEF cells.

Any antigen, including those that induce a T-cell response, can be expressed by the recombinant MVA of the invention. Viral, bacterial, fungal, and cancer antigens are preferred. HIV-1 antigens, Dengue virus antigens, prostate-specific antigen (PSA) and prostatic acid phosphatase (PAP) antigen, HER-2/Neu antigens, anthrax antigens, measles virus antigens, influenza virus, picornavirus, coronavirus and respiratory syncytial virus antigens are particularly preferred antigens. Preferably, the antigen is a foreign antigen or neoantigen.

The invention encompasses methods of making recombinant poxviruses, preferably MVA, comprising inserting a heterologous nucleic acid sequence into a poxvirus such that the heterologous nucleic acid sequence is operably linked to a Pr13.5 promoter.

The invention encompasses use of the recombinant poxviruses of the invention in the manufacture of a medicament or vaccine for the treatment or prevention of infections and diseases of a mammal, including a human.

The invention encompasses use of the recombinant poxviruses of the invention for the treatment or prevention of infections and diseases of a mammal, including a human.

The invention encompasses use of the recombinant poxviruses of the invention as vaccines, particularly for the treatment or prevention of infections and diseases of a mammal, including a human.

Kits Comprising Recombinant MVA

The invention provides kits comprising the recombinant poxviral vector, preferably MVA virus, according to the present invention. The kit can comprise at least one, two, three, four, or more containers or vials of the recombinant poxviral vector, preferably MVA virus, together with instructions for the administration of the virus to a mammal, including a human. The instructions can indicate that the recombinant virus is administered to the mammal, preferably a human, in one or multiple (i.e., 2, 3, 4, 5, 6, etc.) dosages at specific timepoints (e.g., at least 4 weeks, at least 6 weeks, at least 8 weeks after the previous administration). Preferably, the instructions indicate that the recombinant virus is to be administered to a mammal, preferably a human, in at least 1, at least 2, at least 3, or at least 4 dosages.

Methods of Inducing a CD8 T Cell and/or Antibody Response

The invention encompasses methods of inducing a CD8 T cell and/or antibody response in a host. In preferred embodiments, the method comprises administering at least one, two, three, four, or five immunizations of a recombinant poxvirus, preferably MVA, comprising a Pr13.5 promoter to the mammal, including a human.

Administration to a Host

The recombinant poxvirus, preferably MVA, according to the invention can be used for the treatment of a wide range of mammals including humans and even immune-compromised humans. Hence, the present invention also provides a pharmaceutical composition and also a vaccine for inducing an immune response in a mammal, including a human.

The vaccine preferably comprises the recombinant poxvirus, preferably MVA, in a concentration range of $10^4$ to $10^9$ TCID (tissue culture infectious dose)$_{50}$/ml, preferably in a concentration range of $10^5$ to $5 \times 10^8$ TCID$_{50}$/ml, more preferably in a concentration range of $10^6$ to $10^8$ TCID$_{50}$/ml, and most preferably in a concentration range of $10^7$ to $10^8$ TCID$_{50}$/ml, especially $10^8$ TCID$_{50}$/ml.

A preferred vaccination dose for mammal, preferably a human, comprises $10^6$ to $10^9$ TCID$_{50}$, most preferably a dose of $10^7$ TCID$_{50}$ or $10^8$ TCID$_{50}$, especially $10^8$ TCID$_{50}$.

The pharmaceutical composition may generally include one or more pharmaceutically acceptable and/or approved carriers, additives, antibiotics, preservatives, adjuvants, diluents and/or stabilizers. Such auxiliary substances can be water, saline, glycerol, ethanol, oil, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of vaccines, the recombinant poxvirus, preferably MVA, according to the invention can be converted into a physiologically acceptable form. This can be done based on the experience in the preparation of poxvirus vaccines used for vaccination against smallpox (as described by Stickl et al. 1974).

For example, the purified virus can be stored at −80° C. with a titre of $5 \times 10^8$ TCID$_{50}$/ml formulated in about 10 mM Tris, 140 mM NaCl pH 7.4. For the preparation of vaccine shots, e.g., $10^2$-$10^8$ particles of the virus can be lyophilized in 100 µl to 1 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy, the lyophilisate can be dissolved in an aqueous solution, preferably physiological saline or Tris buffer, and administered either systemically or locally, i.e. parenteral, subcutaneous, intravenous, intramuscular, intranasal, or any other path of administration know to the skilled practitioner. The mode of administration, the dose and the number of administrations can be optimized by those skilled in the art in a known manner. However, most commonly a mammal, preferably a human, is vaccinated with a second administration about two weeks to six weeks after the first vaccination administration. Third, fourth, and subsequent administrations will most commonly be about two weeks to six weeks after the previous administration.

The invention provides methods for immunizing mammals, including a human. In one embodiment a subject mammal, which includes rats, rabbits, mice, and humans are immunized comprising administering a dosage of a recombinant MVA to the mammal, preferably to a human. In one embodiment, the first dosage comprises $10^8$ TCID$_{50}$ of the recombinant MVA virus and the second and additional dosages (i.e., third, fourth, fifth, etc.) comprise $10^8$ TCID$_{50}$ of the virus. The administrations can be in a first (priming) dose and a second, or further, (boosting) dose(s).

The immunization can be administered either systemically or locally, i.e. parenterally, subcutaneously, intravenously, intramuscularly, intranasally, or by any other path of administration known to the skilled practitioner.

CD8 T Cell and Antibody Responses

Immunizations with the recombinant MVA of the invention can induce a robust CD8 T cell response. In preferred embodiments, after the first, second, third, fourth, fifth, etc. immunization, the recombinant MVA induces a robust CD8 T cell response in the mammal, preferably a human, against the encoded antigen that is greater than the CD8 T cell response against the immunodominant viral CD8 T cell epitope, e.g. TSYKFESV (SEQ ID NO:5) encoded by the MVA vector. Preferably, after the second, third, fourth, fifth, etc. immunization, an immunodominant T cell response is induced in the mammal, preferably a human, against the encoded antigen. Preferably, after the second, third, fourth, fifth, etc. immunization, the recombinant MVA induces a CD8 T cell response in the mammal, preferably a human, against the encoded antigen that is at least 10%, 15%, 20%, 25%, 30%, or 35% of total CD8 T cells. Preferably, after the second, third, fourth, fifth, etc. immunization, the recombinant MVA increases the CD8 T cell response in the mammal, preferably a human, against the encoded antigen at least 2-, 3-, 4-, 5-, or 10-fold (i.e., from 1% to 2%, 3%, 4%, 5%, or 10% of total CD8 T cells) as compared to the response with the encoded antigen after a single administration or increases the CD8 T cell response in the mammal, preferably a human, against the encoded antigen at least 2-, 3-, 4-, 5-, or 10-fold as compared to the T cell response of a viral antigen (e.g. B8R). Preferably, the recombinant MVA generates a CD8 T cell response in the mammal, preferably a human, against the encoded antigen at least 2-, 3-, 4-, 5-, or 10-fold as compared to the T cell response against a viral antigen (e.g. B8R) after a single administration. Most preferably, the CD8 T cell response in the mammal, preferably a human, against the encoded antigen increases with 2-, 3-, 4-, or 5-, etc. immunizations to a greater extent than the response against a viral late antigen (e.g. B8R).

The level of CD8 T cell response can be determined, for example, by collecting approximately 100-120 µl of blood in FACS/heparin buffer. PBMCs can be prepared by lysing erythrocytes with RBC lysis buffer. PBMCs can then be co-stained in a single reaction for OVA- and B8R-specific CD8 T cells using an anti-CD8α-FITC, CD44-PerCPCy5.5 and MHC class I dextramers complexed with their respective H-2Kb binding peptides, SIINFEKL (SEQ ID NO:4) or TSYKFESV (SEQ ID NO:5). The MHC class I SIINFEKL-dextramer (SEQ ID NO:4) can be labelled with PE and the TSYKFESV-dextramer (SEQ ID NO:5) with APC. Stained cells can be analyzed by flow cytometry on a BD Biosciences BD LSR II system. Ten thousand CD8+ T cells can be acquired per sample.

Alternatively, the level of CD8 T cell response can be determined by collecting blood from an immunized mammal, preferably a human, and separating peripheral blood mononuclear cells (PBMC). These can be resuspended in growth medium containing 5 µg/ml brefeldin A (BFA, "GolgiPlug", BD Biosciences) with 1 µM of test peptides, including peptides against immunodominant MVA epitopes (i.e., TSYKFESV; SEQ ID NO:5) ("B8R") and peptides derived from the expressed neoantigen. The PBMC can then be incubated for 5 h at 37° C. in 5% CO2, harvested, resuspended in 3 ml cold PBS/10% FCS/2 mM EDTA and stored overnight at 4° C. The following day, the PBMC can be stained with antibodies anti-CD8a-Pac-Blue (clone 53-6.7), anti-CD62L-PE-Cy7, anti-CD44-APC-Alexa 750, and anti-CD4-PerCP-Cy5.5 (all antibodies from BD Biosciences). The PBMC can be incubated with appropriate dilutions of the indicated antibodies for 30 min at 4° C. in the dark. After washing, cells can be fixed and permeabilized by using the Cytofix/Cytoperm™ Plus kit (BD Biosciences) according to the manufacturer's instructions. After washing, PBMC can stained for intracellular interferon-γ (IFN-γ) using a FITC-conjugated anti-IFN-γ antibody (BD biosciences) diluted in perm/wash buffer (BD Biosciences). Stained cells can be analysed by flow cytometry.

Immunizations with the recombinant MVA of the invention can induce a robust antibody response. Antibody responses can be measured by ELISA.

Within the context of this invention, a "robust CD8 T cell response" means a higher percentage of neoantigen-specific CD8 T cells than the percentage generated with the same MVA construct containing the PrS promoter (5'AAAAAT-TGAAATTTTATTTTTTTTTTTGGAATATAA 3'; SEQ ID NO:6) after a single immunization. In some embodiments, the CD8 T cell response demonstrates at least 1.5-fold or 2-fold higher neoantigen-specific CD8 T cells than that generated with the same MVA construct containing the PrS promoter (SEQ ID NO:6) after a single immunization.

Within the context of this invention, a "robust antibody response" means an antibody titer that is greater than the antibody titer obtained with the same MVA construct containing the PrS promoter (SEQ ID NO:6) after a single immunization. In some embodiments, the antibody titer is at least 1.5 fold or 2-fold greater than the antibody titer obtained with the same MVA construct containing the PrS promoter (SEQ ID NO:6) after a single immunization.

Whether a recombinant MVA induces a "robust CD8 T cell response" or a "robust antibody response" against a neoantigen can be determined as described in the examples herein. For example, MVA13.5 short and MVA13.5 long both induce a "robust CD8 T cell response" as herein defined. MVA13.5 long induces a "robust antibody response," as herein defined.

Although the method preferably comprises a single administration of the vector, in some embodiments, two, three, four, five, six, seven, or more immunizations of a recombinant MVA can be administered to the mammal, preferably a human.

In preferred embodiments, the encoded antigen is a bacterial, viral, or tumor antigen. Preferably, the antigen is a foreign antigen to the mammal, including a human.

EXAMPLES

Example 1

Generation of MVA Recombinants

HeLa cells were infected with MVA-BN at an MOI of 10 (10 TCID$_{50}$ per cell) and total RNA was prepared 2 and 8 hours post infection. Primers specific for various MVA ORFs were generated and RACE-PCR (FirstChoice® RLM-RACE Kit, Life Technologies, Darmstadt, Germany) was used to generate PCR products representative of the MVA RNAs encoding these ORFs. The PCR products were sequenced to identify the transcription start sites. Based on this information, promoters were identified for the RNAs encoding these ORFs. The MVA promoters for the following ORFs were inserted into MVA constructs (Baur et al., Journal of Virology, Vol. 84 (17): 8743-8752 (2010)) to drive expression of the ovalbumin (OVA) gene: MVA13.5 (CVA022; WR 018), MVA050L (E3L; WR 059), MVA022L (K1L; WR 032), and MVA170R (B3R; WR 185).

Example 2

Promoter-dependent RNA Expression Levels In Vitro

Infection of Hela cells with MVA recombinant viruses at MOI of 10 was done using cold virus attachment on ice for 1 h. After attachment the cells were washed and the zero hour (0 h) time point was collected or cells were incubated at 37° C. for collection of other time points. Samples were collected at 0.5, 1, 2, 4, and 8 h p.i. Cells were homogenized and total RNA was extracted. The RNA was DNAse digested and cDNA was synthesized using oligo(dT) priming. The resulting cDNA preparations were used as template in a Taqman based qPCR reaction for the simultaneous amplification of OVA and actin cDNA. Samples were run in an AB7500 cycler from Applied Biosystem. The results are shown in FIG. 3.

Example 3

Promoter-dependent Protein Expression Levels In Vitro

HeLa cells were cultured in DMEM with 10% FCS. Hela cells were infected with MOI of 10 (10 $TCID_{50}$ per cell) of the recombinant MVA virus. Infected cells were collected at 1, 2, 4, 6, 8, and 24 h p.i., fixed and permeabilized. For each sample, half of the cells were stained for OVA protein using a rabbit anti-chicken OVA antibody and the other half were stained for MVA antigens using a rabbit anti-VACV polyclonal antibody. Samples were analyzed using a FACSCalibur flow cytometry analyzer (BD Biosciences) and FlowJo software. The results are shown in FIG. 4.

Example 4

Mice Immunizations and Bleeds

Groups of mice (C57/B16) were used for the study. Each group received a total of three immunizations. A PBS-injected group served as a control for immune responses. Blood was taken via the tail vein for analysis of immune responses throughout the study.

Mice were immunized i.p. with $10^8$ $TCID_{50}$ of the respective MVA viruses diluted in PBS (300 μL, total volume) at weeks 0, 4 and 8. Bleeds for T cell analysis were performed one week after each immunization and bleeds for antibody analysis were performed three weeks after each immunization.

Example 5

T Cell Staining and Antibody Detection

Approximately 100-120 μl of blood per mouse was collected in FACS/heparin buffer. PBMCs were prepared by lysing erythrocytes with RBC lysis buffer. PBMCs were then co-stained in a single reaction for OVA- and B8R-specific CD8 T cells using an anti-CD8α-FITC, CD44-PerCPCy5.5 and MHC class I dextramers complexed with their respective H-2Kb binding peptides, SIINFEKL (SEQ ID NO:4) or TSYKFESV (SEQ ID NO:5). The MHC class I SIINFEKL-dextramer (SEQ ID NO:4) was labelled with PE and the TSYKFESV-dextramer (SEQ ID NO:5) with APC. Stained cells were analyzed by flow cytometry on a BD Biosciences BD LSR II system. Ten thousand CD8+ T cells were acquired per sample. The results are shown in FIGS. 5-6.

Serum from whole blood was prepared. Ovalbumin ELISA and MVA ELISA were performed to detect specific antibodies (Serazym kit of Seramun Diagnostika GmbH, Heidesee, Germany). The results are shown in FIG. 7.

We claim:

1. A method of inducing a robust CD8 T cell response against a neoantigen in a human comprising administering one or more administrations of a recombinant modified Vaccinia Ankara (MVA) virus to the human;
   wherein the recombinant MVA comprises a Pr13.5 promoter operably linked to a nucleotide sequence encoding the neoantigen,
   wherein the Pr13.5 promoter comprises at least 2 copies of SEQ ID NO:1, and wherein the at the at least 2 copies of SEQ ID NO:1 are separated by 30-40 nucleotides.

2. The method of claim 1, wherein the Pr13.5 promoter comprises SEQ ID NO:2.

3. A recombinant modified Vaccinia Ankara (MVA) virus comprising a Pr13.5 promoter operably linked to a nucleotide sequence encoding a neoantigen,
   wherein the Pr13.5 promoter comprises at least 2 copies of SEQ ID NO:1, and wherein the at the at least 2 copies of SEQ ID NO:1 are separated by 30-40 nucleotides.

4. The recombinant MVA of claim 3, wherein the Pr13.5 promoter comprises SEQ ID NO:2.

* * * * *

SEQUENCE LISTING

```
<160> NUMBER OF SEQ ID NOS: 7

<210> SEQ ID NO 1
<211> LENGTH: 44
<212> TYPE: DNA
<213> ORGANISM: Vaccinia virus

<400> SEQUENCE: 1
taaaaataga aactataatc atataatagt gtaggttggt agta                44

<210> SEQ ID NO 2
<211> LENGTH: 124
<212> TYPE: DNA
<213> ORGANISM: Vaccinia virus

<400> SEQUENCE: 2
taaaaataga aactataatc atataatagt gtaggttggt agtattgctc ttgtgactag   60
agactttagt taaggtactg taaaaataga aactataatc atataatagt gtaggttggt  120
agta                                                              124

<210> SEQ ID NO 3
<211> LENGTH: 273
<212> TYPE: DNA
<213> ORGANISM: Vaccinia virus
```

```
<400> SEQUENCE: 3
tagacgacat gatagaggag gtatccattg acgataatcg tttatcaaca ctaccgttag      60
aaattagaca tttgattttc tcgtacgcgt tcctataaaa atagaaacta taatcatata     120
atagtgtagg ttggtagtat tgctcttgtg actagagact ttagttaagg tactgtaaaa    180
atagaaacta taatcatata atagtgtagg ttggtagtag ggtactcgtg attaatttta    240
ttgttaaact tgtccttaag tcttattaat atg                                  273

<210> SEQ ID NO 4
<211> LENGTH: 8
<212> TYPE: PRT
<213> ORGANISM: Artificial Sequence
<220> FEATURE:
<223> OTHER INFORMATION: OVA peptide

<400> SEQUENCE: 4

Ser Ile Ile Asn Phe Glu Lys Leu
1               5

<210> SEQ ID NO 5
<211> LENGTH: 8
<212> TYPE: PRT
<213> ORGANISM: Artificial Sequence
<220> FEATURE:
<223> OTHER INFORMATION: B8R peptide

<400> SEQUENCE: 5

Thr Ser Tyr Lys Phe Glu Ser Val
1               5

<210> SEQ ID NO 6
<211> LENGTH: 37
<212> TYPE: DNA
<213> ORGANISM: Artificial Sequence
<220> FEATURE:
<223> OTHER INFORMATION: Synthetic Promoter

<400> SEQUENCE: 6
aaaaattgaa attttatttt ttttttttgg aatataa                              37

<210> SEQ ID NO 7
<211> LENGTH: 16
<212> TYPE: DNA
<213> ORGANISM: Artificial Sequence
<220> FEATURE:
<223> OTHER INFORMATION: Synthetic Promoter

<400> SEQUENCE: 7 aattttaat atataa                                                      16
```

UNITED STATES PATENT AND TRADEMARK OFFICE
CERTIFICATE OF CORRECTION

| | | |
|---|---|---|
| PATENT NO. | : 9,828,414 B2 | Page 1 of 1 |
| APPLICATION NO. | : 14/437939 | |
| DATED | : November 28, 2017 | |
| INVENTOR(S) | : Robin Steigerwald and Kay Brinkmann | |

It is certified that error appears in the above-identified patent and that said Letters Patent is hereby corrected as shown below:

In the Claims

Claim 3 (Column 18, Line 61): "at the" should be deleted

Signed and Sealed this
Twenty-seventh Day of February, 2024

Katherine Kelly Vidal
*Director of the United States Patent and Trademark Office*